United States Patent [19]

Liu

[11] 4,335,480
[45] Jun. 22, 1982

[54] ELECTRIC ROTARY TOOTHBRUSH

[76] Inventor: Poo-Sung Liu, 2009 Hillview Rd., Lawrence, Kans. 66044

[21] Appl. No.: 173,530

[22] Filed: Jul. 30, 1980

[51] Int. Cl.³ .............................................. A46B 13/02
[52] U.S. Cl. ..................................................... 15/23
[58] Field of Search .................... 15/23, 24; 128/62 A; 51/170 PT

[56] References Cited

U.S. PATENT DOCUMENTS

| | | | |
|---|---|---|---|
| 1,822,631 | 9/1931 | Roig | 15/23 |
| 1,927,566 | 9/1933 | Hawk | 15/23 |
| 2,533,106 | 12/1950 | Grover | 15/23 |
| 2,904,804 | 9/1959 | Odessey | 15/23 X |
| 3,551,932 | 1/1971 | Grossman | 15/23 |

*Primary Examiner*—Edward L. Roberts
*Attorney, Agent, or Firm*—Leitner, Palan, Martin & Bernstein

[57] ABSTRACT

An electric rotary toothbrush having an integral stem and brush guard housing within which is an axially moveable brush drive shaft and a removable brush. The brush drive shaft is manually controlled for axial movement by a control knob located on the stem and brush guard housing to lock the brush so that it is rotatably mounted on both sides thereof within the stem and brush guard housing and to allow removal of the brush from the housing.

8 Claims, 6 Drawing Figures

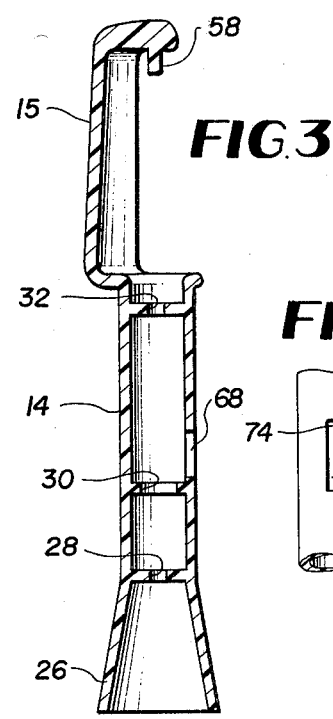
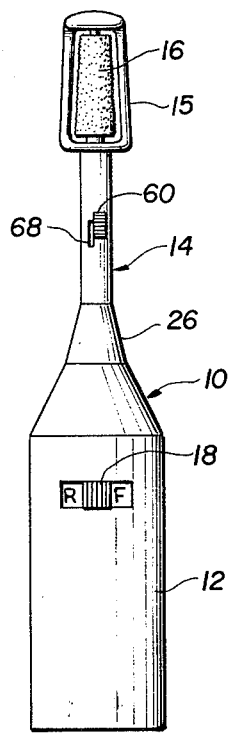
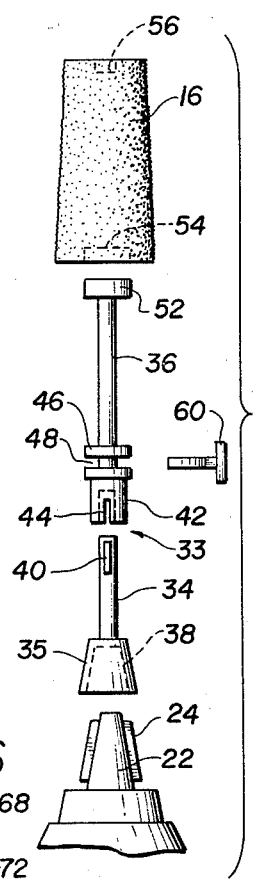
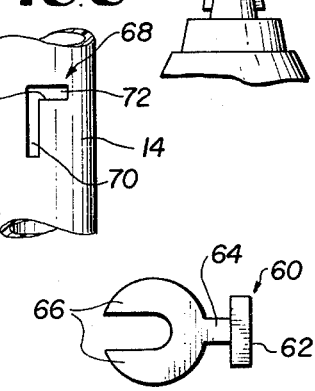
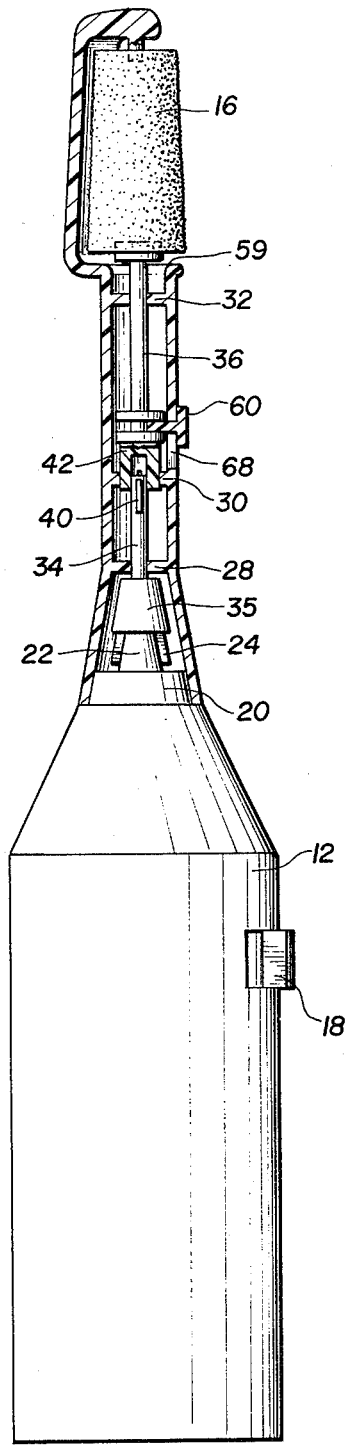

ELECTRIC ROTARY TOOTHBRUSH

BACKGROUND OF THE INVENTION

The present invention relates generally to electric toothbrushes, and more particularly to an electric toothbrush having a power driven rotary brush.

The use of electric toothbrushes has become very popular as means for achieving simple and efficient overall dental care. Prior art electric rotary toothbrushes provide a rotary brush with axial support on one end. That is, there is not any rotational support on the end of the rotary brush furtherest from the rotary drive connection. As a result of this design, the rotary brush has little stability. In addition, the interconnection of the drive shaft and rotary brush must necessarily be specially designed so that both a drive and mount connection are provided. This special design results in the increased cost of manufacture of the electric rotary toothbrush.

Further, prior art electric rotary toothbrushes generally do not provide for easy removal of the rotary brush or the rotary brush guard. It is advantageous to have an electric rotary toothbrush in which the rotary brush and/or the rotary brush guard can be easily replaced by another rotary brush and/or rotary brush guard so that members of the same family may share a single toothbrush and each have his or her own personal brush.

Prior art toothbrushes that do allow for brush removal are not adequate. By the continued mounting and unmounting of the brush to the motor drive in conventional electric rotary toothbrushes, the interconnection mechanism has been known to wear, resulting in an unstable condition such that the brush cannot be maintained in a rotatably connected mode and in some instances may actually break.

Examples of the prior art include U.S. Pat. No. 3,739,416 to Kurachi in which the rotary brush may be removed only if the brush guard is pivoted or snapped to an open position. In U.S. Pat. No. 3,161,899 to Poizat, the entire arrangement including the stem, rotary brush casing, and rotary can be removed but only as a unit. To remove the rotary brush itself requires the removal of screw 24.

U.S. Pat. No. 3,551,032 to Grossman provides a brush 22 having an elongated stem 20 permanently connected thereto. Sleeve 26 must be opened in order to remove the brush 22 and its elongated stem 20. There is proven need for a rotary electric toothbrush that not only provides rotational support on both ends of its axis, but in addition, can be easily removed and replaced without having to resort to complicated toothbrush housing structure.

SUMMARY OF THE INVENTION

Accordingly, it is an object of this invention to provide an electrical rotary toothbrush in which the brush may be easily inserted and removed.

It is another object of this invention to provide an improved rotary electric toothbrush having a unitary stem and brush guard housing wherein the rotary brush is supported for rotary movement on both sides of its rotational axis.

It is yet another object of this invention to provide a rotary electric toothbrush in which the rotary brush may be inserted or removed without disassembling the stem and brush guard housing and still provide substantial support on its rotational axis.

According to the invention, there is provided an electric rotary toothbrush having a brush that is mounted for rotation on both sides of its rotational axis and is removeable without disassembly or movement of any part of the toothbrush housing. In order to accomplish such a design, an axially moveable brush drive shaft is provided on the interior of the housing that is manually actuated by a control knob mounted on the housing to provide a locked position of the brush drive shaft wherein the rotary brush is rotationally supported on both sides of its axis and an unlocked position wherein the brush may be removed. As a result of the novel design of the axially moveable brush drive shaft and two-end rotational support of the brush, the housing for the brush and its drive shaft may be formed from an integral unit.

Other objects, advantages and novel features of the present invention will become apparent from the following detailed description of the invention when considered in conjunction with the accompanying drawings.

BRIEF DESCRIPTION OF THE DRAWINGS

FIG. 1 is a front plan view of the inventive toothbrush fully assembled.

FIG. 2 is a side plan view of the inventive toothbrush handle and side cross-section of the stem and brush guard section fully assembled.

FIG. 3 is a cross-section of the stem and brush guard housing of the inventive toothbrush.

FIG. 4 is an exploded view of the rotary brush and the driven rotary shaft.

FIG. 5 is a plan view of the moveable lever control arm.

FIG. 6 is an enlarged view of the opening in the stem housing in which the moveable lever control arm is placed.

DESCRIPTION OF THE PREFERRED EMBODIMENTS

Referring to FIGS. 1 and 2, electric toothbrush 10 is shown to consist of handle section 12, stem 14, brush guard 15 and rotary brush 16. Handle section 12 which does not form any part of the invention contains a reversible motor powered by a rechargeable battery or other suitable power source (not shown) and actuated by switch 18 so that brush 16 may operate in either a clockwise or counter-clockwise direction. Obviously the battery does not have to be rechargeable. Located on the top of handle 12 is a tapered conical stem housing receiving portion 20 best seen in FIG. 2. Conical drive member 22 is connected to the motor driven shaft in the housing of the handle (not shown) and has provided thereon flanges 24.

Housing portion 26 of stem 14 is shaped to press-fit over stem housing receiving portion 20 of handle 12. Stem housing 14 and brush guard 15 are formed from molded plastic as an integral element provided with internal annular ribs 28, 30, and 32, as best seen in FIG. 3. Positioned on the interior of stem housing 14 and shown in FIG. 4 is a shaft 33. In the preferred embodiment, shaft 33 consists of two main shaft sections 34 and 36. It is understood that a single shaft may be provided as explained in greater detail below. The bottom end 35 of shaft section 34 is constructed to fit over conical member 22 and has on the interior thereof slotted receiving grooves 38 to accommodate flanges 24. With bottom end 35 of shaft section 34 interconnected with conical member 22, a driving connection is established such that rotation of member 22 causes rotation of shaft section 34. Located on the upper end of shaft section 34 are flanges 40. Shaft section 36 is constructed with base portion 42 having aligned axial grooves 44 shaped to slidingly receive flanges 40 of shaft section 34 so that the rotation of shaft section 34 will cause rotation of shaft section 36. Adjacent the base portion 42 is an enlarged portion 46 having an annular recess 48. At the top of shaft section 36 is an enlarged portion 52 constructed to physically mate with portion 54 of rotary brush 16 so that when portion 52 is interlocked with portion 54 rotation of shaft section 36 will cause rotation of brush 16. Brush guard 15 has a member 58 constructed to mate with portion 56 of rotary brush 16 to provide rotational support for brush 16. It is understood that the interlocking of portions 52 and 54 and portions 56 and 58 may be of any suitable design and does not form a part of the invention. The important feature is that the brush 16 is removably and rotatably interconnected at its top to the brush guard housing and removably and rotatably interconnected to be driven by the shaft section 36.

Referring to FIG. 5, control knob 60 is shown from a top plan view as including handle portion 62, neck 64, and arms 66. Control knob 60 is used to control and to maintain shaft section 36 in one of two desired positions, namely, a brush lock, or raised position and a brush removal position. The control knob 60 is positioned with neck 64 traversing an opening 68 of stem housing 14 and arms 66 lying in annular recess 48 of the shaft 36. Opening 68 as best seen in FIG. 6 is in the shape of an inverted L and includes a vertical slot 70 and horizontal slot 72 having a ledge 74. The vertical slot permits vertical movement of shaft 36 relative to shaft 34 and the ledge 74 provides a raised lock position. Since the raised position is the operating position of shaft 36, groove 44 must be long enough to accommodate the axial or vertical motion while maintaining a driving relationship with shaft 34.

With the electric rotary toothbrush 10 assembled, shaft sections 34 and 36 are located in the interior of stem housing 14. Annular rib 28 serves to keep shaft section 34 in axial alignment with shaft section 36 and conical member 22. Annular ribs 30 and 32 serve to maintain shaft section 36 in axial alignment with brush 16 and shaft section 34. Control knob 60 is inserted in opening 68 of stem 14 such that arms 66 fit into annular recess 48. Flanges 24 of conical member 22 is accomodated in grooves 38 of shaft section 34 to provide a driving relationship with the motor.

The operation of electric rotary toothbrush 10 and control knob 60 fully assembled can be explained as follows. With control knob 60 in the raised and locked position shown in FIG. 1, the neck 64 is located in horizontal slot 72 of opening 68 and rests locked on ledge 74. Arms 66 of control knob 60 is in annular recess 48 and maintains shaft section 36 in a raised position. Portion 52 of shaft section 36 is maintained in its mated condition with portion 54 of brush 16 and portion 56 of brush 16 is maintained in its mated condition with portion 58 of brush guard 15. Flanges 40 of shaft section 34 is maintained in the lower interlocking portion of grooves 44 of shaft section 36. Actuation of switch 18 causes rotation of conical member 22, shaft sections 34 and 36 and rotary brush 16.

With control knobs 60 in the position discussed above, shaft 36 is maintained in its raised and lock position. Brush 16 is thus provided with rotational support on both ends thereof at portions 54 and 56. Further, there is no possibility of inadvertent removal of brush 16 due to the positive interconnection of portion 52 of shaft section 36 with portion 54 of the brush and the interconnection of portion 56 of the brush with portion 58 of the guard 15.

When it is desired to remove brush 16, control knob 60 is manually rotated so that neck 64 is first slid horizontally toward the vertical slot 70 and then in a downward direction so that at the end of its travel control knob 60 is positioned at the bottom of vertical slot 70. The downward movement of control knob 60 results in arms 66 causing shaft section 36 to move downward. Grooves 44 of shaft section 36 ride on flanges 40 of shaft section 34 such that at the end of the downward movement of shaft section 36 flanges 40 are positioned in the upper portion of respective grooves 44. It should be appreciated that the flanges 40 are always positioned in grooves 44 so that when control knob 60 is returned to its original position shown in FIG. 1, a driving connection between flanges 40 and grooves 44 is maintained.

With the control knob 60 positioned such that neck 64 is on the bottom of vertical slot 70, shaft section 36 is lowered so that the brush portion 56 becomes disconnected with portion 58 of guard 15. Similarly, the guard housing is designed with shoulder 59 to retain the bottom of the toothbrush so that the lowering of the shaft section 36 disconnects shaft portion 52 and rotary brush portion 54 so that the brush can be easily removed. It is evident that another brush of the same size and configuration can replace brush 16 if it is so desired.

In an alternative embodiment of the invention (not shown) shaft 33 may be a single piece. In that instance, an equivalent to control knob 60 and the associated structure of enlarge portion 42 can be located at the lower end of the proposed single shaft. Conical member 22 and its associated flanges 24 can be modified to be the functional equivalent of flange 40 of shaft section 34. Also, control knob 60 and enlarged portion 42 may be at the center of the single shaft if desired. The two-piece drive shaft is preferred because the brush can be easily removed without disassembly of the toothbrush guard from the handle and because the parts which are moved during brush insertion and removal and thus the parts most susceptible to wear are the easily replaceable two-piece drive shaft and not its connection with the motor. Thus, the most inexpensive part wears first. This is a substantial advantage over prior art systems.

From the preceding description of the preferred embodiments, it is evident that the objects of the invention are attained in that a rotary electric toothbrush is provided in which the brush has rotational support at both ends of its axis and can be easily removed without disassembly of the toothbrush housing. Although the invention has been described and illustrated in detail, it is to be clearly understood that the same is by way of illustration and example only and is not to be taken by way of limitation. The spirit and scope of this invention are to be limited by the terms of the appended claims.

What is claimed is:
1. An electric rotary toothbrush comprising:
a housing;
an electric motor mounted in said housing;
a brush drive shaft rotatably mounted in said housing;
a rotary brush rotatably mounted in said housing;

a first support means connected to said brush drive shaft for rotatably supporting one end of said rotary brush;

a second support means in said housing for rotatably supporting the other end of said brush;

a control means mounted on said housing and connected to said brush drive shaft for determining the axial position of said first support means; and an opening in said housing in which said control means moves, said opening having a first axial portion and a second transverse portion, said control means being positioned in said second portion of said opening to lock said first support means into engagement with said rotary brush, and said control means movable in said first portion of said opening to disengage said first support means from said rotary brush.

2. The electric toothbrush of claim 1 wherein said second portion includes a ledge upon which said control means rests to be locked.

3. The electric toothbrush of claim 1, wherein said housing includes a handle section and a brush guard and stem section detachably mounted to said handle section.

4. The electric toothbrush of claim 3, wherein said brush guard and stem housing section comprises an integral housing having an annular rib means for maintaining said rotary brush drive shaft in axial alignment with said rotary brush.

5. The electric toothbrush of claim 3, wherein said second support means is located on said brush guard and stem housing section.

6. The electric toothbrush of claim 1, wherein said brush drive shaft comprises first and second separate axially aligned sections, said first section being movable in an axial direction.

7. The electric toothbrush of claim 1, where said electric motor is reversible and is powered by rechargeable batteries.

8. An electric rotary toothbrush comprising:

a handle housing;

an integral brush and stem housing attached to said handle housing;

a motor mounted with said handle housing;

a brush drive shaft mounted within said brush guard and stem housing having first and second sections axially movable with respect to each other, said first section being connected to said motor and said second section being connected to said brush;

a rotary brush rotatably mounted on both ends of its rotary axis within said brush guard and stem housing;

an opening in said brush guard and stem housing having first and second portions;

a control means positioned in said opening and connected to said second section of said brush drive shaft;

said first portion of said opening in said brush guard and stem housing section maintaining said control means locked in its first position to lock said rotary brush in said housing;

said first brush drive shaft section being movable in a direction away from said rotary brush when said control means is in its said second portion of said opening such that said rotary brush may be removed.

* * * * *